US008153862B2

(12) United States Patent
Kim et al.

(10) Patent No.: US 8,153,862 B2
(45) Date of Patent: Apr. 10, 2012

(54) CYTOCHROME P450 GENE FOR INCREASING SEED SIZE OR WATER STRESS RESISTANCE OF PLANT

(75) Inventors: Ho Bang Kim, Seoul (KR); Sang Bong Choi, Seongnam-si (KR)

(73) Assignee: Myongji University Industry and Academia Cooperation, Yongin-si (KR)

( * ) Notice: Subject to any disclaimer, the term of this patent is extended or adjusted under 35 U.S.C. 154(b) by 211 days.

(21) Appl. No.: 12/523,780

(22) PCT Filed: Jan. 15, 2008

(86) PCT No.: PCT/KR2008/000250
§ 371 (c)(1),
(2), (4) Date: Jul. 20, 2009

(87) PCT Pub. No.: WO2008/088161
PCT Pub. Date: Jul. 24, 2008

(65) Prior Publication Data
US 2010/0281576 A1    Nov. 4, 2010

(30) Foreign Application Priority Data

Jan. 19, 2007  (KR) ........................ 10-2007-0005864
Jan. 19, 2007  (KR) ........................ 10-2007-0005866
Jan. 19, 2007  (KR) ........................ 10-2007-0005870

(51) Int. Cl.
*A01H 5/00* (2006.01)
*A01H 5/10* (2006.01)
*C12N 15/82* (2006.01)
(52) U.S. Cl. ........................................ 800/290; 800/298
(58) Field of Classification Search ........................ None
See application file for complete search history.

(56) References Cited

U.S. PATENT DOCUMENTS 4,940,838 A    7/1990    Schilperrort et al.

FOREIGN PATENT DOCUMENTS

| EP | 0116718 B1 | 5/1990 |
| EP | 0120516 B1 | 10/1991 |
| EP | 0301316 B1 | 6/1993 |
| WO | 98/40470 A2 | 9/1998 |

OTHER PUBLICATIONS

NCBI accession No. AAM97067, Aug. 27, 2002.*
GenBank Assession No. AAM97067.1.*
GenBank Assession No. BT000225.1.*
Chapple (Annu. Rev. Plant Physiol.Plant Mol. Biol. 1989, 49:311-343).*
Anzenbacher et al (CMLS, Cell. Mol. Life Sci. 58 (2001) 737-747.*
Ito et al (The Plant Cell, vol. 12, 1541-1550, Sep. 2000).*
R.D. Shillito, et al., "High Efficiency Direct Gene Transfer to Plants", Bio/Technology vol. 3: Dec. 1985, Switzerland.
U.K. Laemmli, "Cleavage of Structural Protein during the Assembly of the Head of Bacteriophage T4", Nature vol. 227: 680-685, Aug. 15, 1970.
T.M. Klein, et al., "High-velocity microprojectiles for delivering nucleic acids into living cells", Nature vol. 327: 70-73 (USA) May 7, 1987.
Andrew P. Gleave, "A versatile binary vector system with a T-DNA organizational structure conducive to efficient integration of cloned DNA into the plant genome", Plant Molecular Biology 20: 1203-1207 (New Zealand) 1992.
Clint Chapple, "Molecular-Genetic Analysis of Plant Cytochrome P450-Dependent Monooxygenases", Annu. Rev. Plant Physiol. Plant Mo. Biol. 49: 311-343 (USA) 1998.
Steven J. Clough, et al., "Floral dip: a simplified method for Agrobacterium-mediated transformation of *Arabidopsis thaliana*", The Plant Journal 16(6): 735-743 (USA) 1998.
Yee Hwa Yang, et al., "Normalization for cDNA microarray data: a robust composite method addressing single and multiple slide systematic variation", Nucleic Acids Research vol. 30 No. 4e15 (USA) 2002.
Ho Bang Kim, et al., "A Type-1 Chalcone Isomerase mRNA is highly expressed in the root nodules of *Elaeagnus umbellata*", Journal of Plant Biology vol. 46(4): 263-270 (Korea) Dec. 2003.
Anne Crossway, et al., "Integration of foreign DNA following microinjection of tobacco mesophyll protoplasts", Mol Gen Genet 202: 179-185 (USA) 1986.
F.A. Krens, et al., "In vitro transformation of plant protoplasts with Ti-plasmid DNA", Nature vol. 296: 72-74 (The Netherlands) Mar. 4, 1982.
I. Negrutiu, et al., "Hybrid genes in the analysis of transformation conditions", Plant Molecular Biology 8: 363-373 (The Netherlands) 1987.
C.C. Dalton et al., "Iron phosphate precipitaiton in Murashige and Skoog media", Physiol. Plant. 57: 472-476. Copenhagen 1983.
Stomp A-M (1992), "Histochemical localization of beta-glucuronidase", in S.R. Gallagher ed, GUS protocols: Using the GUS gene as a reporter of gene expression, Academic Press, San Diego, CA, pp. 103-113.
Sambrook, T. et al., (1989) Molecular Cloning—A Laboratory Manual (second edition), vol. 1-3, Cold Spring Harbor Laboratory, Cold Spring.
NCBI sequence database accession No. AAM97067. Aug. 27, 2002.

(Continued)

*Primary Examiner* — Anne Grunberg
*Assistant Examiner* — Lee Visone
(74) *Attorney, Agent, or Firm* — Kile Park Goekjian Reed & McManus PLLC

(57) ABSTRACT

The present invention relates to cytochrome P450 protein originating from *Arabidopsis thaliana* which can be used for increasing seed size or storage protein content in seed or for increasing water stress resistance of plant, a gene encoding said protein, a recombinant plant expression vector comprising said gene, a method of increasing seed size or storage protein content in seed and a method of increasing water stress resistance of plant by using said vector, plants produced by said method and transgenic seed of said plants. According to the present invention, by using cytochrome P450 gene of the present invention, seed size or storage protein content in seed can be increased or water stress resistance of plant can be increased.

5 Claims, 8 Drawing Sheets

OTHER PUBLICATIONS

NCBI sequence database accession No. BT000225. Sep. 19, 2002.

Toshiro Ito and Elliot M. Meyerowitz, "Overexpression of a Gene Encoding a Cytochrome P450, CYP78A9, Induces large and seedless fruit in *Arabidopsis*", The Plant Cell, vol. 12(9): 1541-1551 (US) 2000.

Kazumaru Miyoshi, et al., "PLASTOCHRON1, a timekeeper of leaf initiation in rice, encodes cytochrome p450", P.N.A.S., vol. 101(3): 875-880 (JP) 2004.

* cited by examiner

US 8,153,862 B2

CYTOCHROME P450 GENE FOR INCREASING SEED SIZE OR WATER STRESS RESISTANCE OF PLANT

TECHNICAL FIELD

The present invention relates to cytochrome P450 protein originating from *Arabidopsis thaliana* which can be used for increasing seed size or storage protein content in seed or for increasing water stress resistance of plant, a gene encoding said protein, a recombinant plant expression vector comprising said gene, a method of increasing seed size or storage protein content in seed and a method of increasing water stress resistance of plant by using said vector, plants produced by said method and transgenic seed of said plants.

BACKGROUND ART

Cytochrome P450 catalyzes many enzymatic reactions for various kinds of substrates, i.e., an oxidative, peroxidative, and reductive metabolism of endogenous and xenobiotic substrate. Specifically, plant P450 participates in various biochemical pathways for the synthesis of plant products including phenylpropanoids, alkaloids, terpenoids, lipids, cyanogenic glycosides and glucosinolates (Chapple, Annu. Rev. Plant Physiol. Plant Mol. Biol. 1989, 49: 311-343).

Cytochrome P450 is also known as P450 hemi-thiolate protein and functions as a final oxidizing enzyme in multi-component electron transfer chains that is called P450-comprising monooxygenase system. As a specific catalytic reaction, it includes demethylation, hydroxylation, epoxidation, N-oxidation, sulfooxidation, N-, S- and O-dealkylation, deamination, desulfation, and reduction of azo, nitro and N-oxide group.

Various roles of P450 enzyme of *nicotiana* plants are related to a diversity of plant metabolites such as phenylpropanoids, alkaloids, terpenoids, lipids, cyanogenic glycosides, and glucosinolates and a host of other chemical entities. During the last couple of years, it has been confirmed that some of the P450 enzymes have an effect on a constitution of plant metabolites in plants.

Based on the-above described prior art, inventors of the present invention found that, while studying the functions of cytochrome P450, cytochrome P450 originating from *Arabidopsis thaliana* can improve seed size of plants or storage protein content in plants or increase water stress resistance of plants, and therefore completed the present invention.

DETAILED DESCRIPTION OF THE INVENTION

Technical Goal of the Invention

In the present invention, the function of cytochrome P450 protein, which originates from *Arabidopsis thaliana*, in plants is to be investigated.

Disclosure of the Invention

In order to address the above-described problems, the present invention provides cytochrome P450 protein originating from *Arabidopsis thaliana* which can be used for increasing seed size of plants or storage protein content in seed, or for increasing water stress resistance of plant.

Further, one object of the present invention is to provide a gene encoding said cytochrome P450 protein.

Further, one object of the present invention is to provide a recombinant plant expression vector comprising said gene.

Further, one object of the present invention is to provide a method of increasing seed size or storage protein content in seed, and a method of increasing water stress resistance of plant by using said vector.

Still further, one object of the present invention is to provide plants produced by said method and transgenic seed of said plants.

Effect of the Invention

According to the present invention, seed size or storage protein content in seed can be increased or water stress resistance of plant can be increased by using cytochrome P450 gene of the present invention.

BEST MODE FOR CARRYING OUT THE INVENTION

Figure 1:
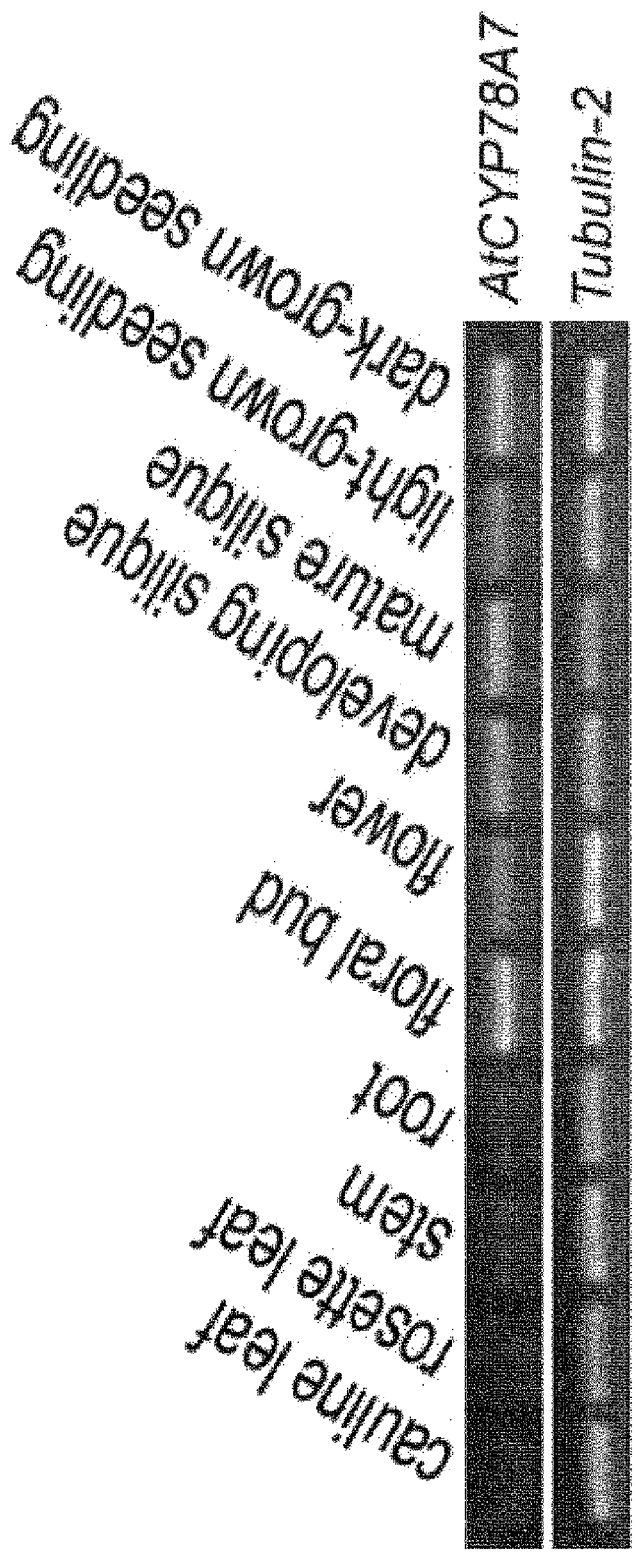
FIG. 1 shows RT-PCR analysis of AtCYP78A7 expression in different tissues of *Arabidopsis thaliana*.

In order to achieve the object of the present invention described above, the present invention provides cytochrome P450 protein originating from *Arabidopsis thaliana* having an amino acid sequence of SEQ ID NO: 1, which can be used for increasing seed size of plants or storage protein content in seed, or for increasing water stress resistance of plant.

The present invention relates to the use of cytochrome P450 protein originating from *Arabidopsis thaliana*. Specifically, said protein can be used for increasing seed size of plants or storage protein content in seed, or for increasing water stress resistance of plant. Said storage protein in seed can be 12S acidic storage protein in seed, 12S basic storage protein in seed, or 2S storage protein in seed, but is not limited thereto.

For cytochrome P450 protein according to one embodiment of the present invention, it can comprise the amino acid sequence of SEQ ID NO: 1. In addition, variants of said amino acid sequence are within the scope of the present invention. Variants comprise an amino acid sequence that can be changed but having properties functionally and immunologically similar to the amino acid sequence of SEQ ID NO: 1. Specifically, cytochrome P450 protein may comprise an amino acid sequence with at least 70%, preferably at least 80%, more preferably at least 90%, still more preferably at least 95% homology with the amino acid sequence of SEQ ID NO: 1.

The present invention further provides a gene (AtCYP78A7) which encodes cytochrome P450 protein originating from *Arabidopsis thaliana* having an amino acid sequence of SEQ ID NO: 1 that can be used for increasing seed size of plants or storage protein content in seed, or for increasing water stress resistance of plant. Preferably, said gene comprises the nucleotide sequence of SEQ ID NO: 2. In addition, variants of said nucleotide sequence are within the scope of the present invention. Variants comprise a nucleotide sequence that can be changed but having properties functionally and immunologically similar to the nucleotide sequence of SEQ ID NO: 2. Specifically, the gene encoding cytochrome P450 protein may comprise a nucleotide sequence with at least 70%, preferably at least 80%, more preferably at least 90%, still more preferably at least 95% homology with the nucleotide sequence of SEQ ID NO: 2.

Said "sequence homology %" for a certain polynucleotide and polypeptide is identified by comparing a comparative region with two sequences that are optimally aligned. In this regard, a part of the polynucleotide or polypeptide sequence in comparative region may comprise an addition or a deletion (i.e., a gap) compared to a reference sequence (without any addition or deletion) relative to the optimized alignment of the two sequences.

Said percentage is obtained by identifying the number of sites wherein nucleotide bases or amino acid residues are present for both sequences to be compared, obtaining the number of matching sites therefrom, dividing the obtained number by the total number of the sites in comparative region, and multiplying the resulting value with 100, thus yielding percentage of sequence homology. The optimum alignment for such comparison can be carried out either by computer implementation with a known processing mode (for example, GAP, BESTFIT, FASTA and TFAST in the Wisconsin Genetics Software Package, Genetics Computer Group (GCG), 575 Science Dr., Madison, Wis., or BlastN and BlastX available from the National Center for Biotechnology Information) or by determination.

The terms "substantial identity" or "substantial similarity" that are used herein mean that, a polypeptide comprises a sequence which can hybridize to a target polypeptide under stringent condition. The stringent condition indicates 2×SSC solution and the temperature of 65° C.

"Substantially similar" polypeptides share said sequence except that the position of different residues may vary with a conservative change in amino acid residues. Conservative amino acid substitution indicates an interchangeability among amino acid residues that have a similar side chain. For example, amino acid group having an aliphatic side chain includes glycine, alanine, valine, leucine and isoleucine, amino acid group having an aliphatic hydroxyl side chain includes serine and threonine, and amino acid group having an amide-comprising side chain includes asparagine and glutamine, amino acid group an aromatic side chain includes phenylalanine, tryptophane, and tyrosine, amino acid group having a basic side chain includes lysine, arginine, and histidine and amino acid group having sulphur-containing side chain includes cysteine and methionine.

Substantial identity of a polynucleotide sequence means that the polynucleotide comprises a sequence with at least 70%, preferably at least 80%, more preferably at least 90%, still more preferably at least 95% sequence identity. According to another definition, when two nucleotide molecules are specifically hybridized to each other under stringent condition, their nucleotide sequences are substantially identical to each other. Stringent condition is dependent on nature of a sequence and may vary under other different conditions. Generally, at defined ionic strength and pH, the stringent condition is selected to have a temperature that is about 10° C. lower than melting point (Tm) of a specific sequence. Tm is a temperature at which 50% of a target sequence is hybridized to a probe having complete match (at defined ionic strength and pH). Tm of a hybridization complex, which is determined by both of probe length and base composition, can be calculated according to the information described in literature (Sambrook, T. et al., (1989) Molecular Cloning—A Laboratory Manual (second edition), Volume 1-3, Cold Spring Harbor Laboratory, Cold Spring). Typically, the stringent condition for Southern blot analysis includes washing with 0.2× SSC at 65° C. For a preferred oligonucleotide probe, the washing condition is typically at 42° C. with 6×SSC.

According to one embodiment of the present invention, cytochrome P450 encoding gene may further comprise a promoter sequence consisting of the nucleotides sequence of SEQ ID NO: 3 for cytochrome P450 encoding gene. After the fusion of GUS gene to said promoter sequence and the subsequent expression of the resulting gene in plants, it was found that said gene is strongly expressed in cotyledon and apical meristem of dark-germinating/light-germinating seedlings, as well as in floral bud, flower, axillary bud, or embryo under the development.

In order to achieve another object of the present invention, the present invention provides a recombinant plant expression vector which comprises the gene according to the present invention.

The term "recombinant" indicates a cell which replicates a heterogeneous nucleotide or expresses said nucleotide, a peptide, a heterogeneous peptide, or a protein encoded by a heterogeneous nucleotide. Recombinant cell can express a gene or a gene fragment that are not found in natural state of cell in a form of a sense or antisense. In addition, a recombinant cell can express a gene that is found in natural to state, provided that said gene is modified and re-introduced into the cell by an artificial means.

The term "vector" is used herein to refer DNA fragment (s) and nucleotide molecules that are delivered to a cell. Vector can replicate DNA and be independently reproduced in a host cell. The terms "delivery system" and "vector" are often interchangeably used. The term "expression vector" means a recombinant DNA comprising a desired coding sequence and other appropriate nucleotide sequences that are essential for the expression of the operatively-linked coding sequence in a specific host organism. Promoter, enhancer, termination signal and polyadenylation signal that can be used for an eukaryotic cell are all publicly well known.

A preferred example of plant expression vector is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) is currently used for transferring a hybrid gene to protoplasts that can produce a new plant by appropriately inserting a plant cell or hybrid DNA to a genome of a plant. Especially preferred form of Ti-plasmid vector is a so called binary vector which has been disclosed in EP 0 120 516 B1 and U.S. Pat. No. 4,940,838. Other vector that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be advantageous especially when a plant host cannot be appropriately transformed.

Expression vector would comprise at least one selection marker. Said selection marker includes dehydrofolate reductase or neomycin-resistant gene for culture of eukaryotic cells. The selection marker that is most widely used for plant transformation is neomycin phosphotransferase II (nptII) gene which is separated from Tn5 and hygromycin phosphotransferase gene which has a resistance to hygromycin, an antibiotic.

For the plant expression vector according to one embodiment of the present invention, a promoter can be any of CaMV 35S, actin, ubiquitin, pEMU, MAS or histone promoters, but not limited thereto. The term "promoter" means a DNA molecule to which RNA polymerase binds in order to initiate its transcription, it corresponds to a DNA region upstream of a structural gene. The term "plant promoter" indicates a promoter which can initiate transcription in a plant cell. The term "constitutive promoter" indicates a promoter which is active in most of environmental conditions and development states or cell differentiation states. Since a transformant can be selected with various mechanisms at various stages, a constitutive promoter can be preferable for the present invention. Therefore, a possibility for choosing a constitutive promoter is not limited herein.

The terminator can be nopaline synthase (NOS) or rice α-amylase RAmy1 A terminator, but not limited thereto. Regarding the necessity of terminator, it is generally known that such region can increase a reliability and an efficiency of transcription on plant cells. Therefore, the use of terminator is highly preferable in view of the contexts of the present invention.

In order to achieve another object of the present invention, the present invention provides a method of increasing seed size or storage protein content in seed and a method of increasing water stress resistance of plant, comprising a step of transforming plant cells with the recombinant plant expression vector of the present invention to overexpress cytochrome P450 gene. Preferably, said plant can be selected from a group consisting of *Arabidopsis thaliana*, rice, rapeseed, wheat, barley, corn, soybean, potato, red bean, oat and millet, but not limited thereto.

The term "plant tissue" can be either differentiated or undifferentiated plant tissue, including root, stem, leaf, pollen, seed, cancerous tissue and cells having various shape that are used for culture, i.e., single cell, protoplast, bud and callus tissue, but not limited thereto. Plant tissue can be in plants or in a state of organ culture, tissue culture or cell culture.

The term "plant cell" includes in planta plant cell, and further includes plant cell and protoplast in culture state.

Plant transformation means any method by which DNA is delivered to a plant. Such transformation method does not necessarily have a period for regeneration and/or tissue culture. Transformation of plant species is now quite general not only for dicot plants but also for monocot plants. In principle, any transformation method can be used for introducing a hybrid DNA of the present invention to an appropriate progenitor cells. It can be appropriately selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microinjection method for plant components (Crossway A. et al., 1986, Mol. Gen. Genet. 202, 179-185), a particle bombardment method for various plants components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. A preferred method in the present invention includes *Agrobacterium* mediated DNA transfer. In particular, so called binary vector technique as disclosed in EP A 120 516 and U.S. Pat. No. 4,940,838 can be preferably adopted for the present invention.

In order to achieve another object of the present invention, the present invention provides plants of which seed size or storage protein content in seed are increased or water stress resistance is increased. By transforming plant cells using the method of the present invention, cytochrome P450 gene can be overexpressed, resulting that seed size or storage protein content in seed are increased or water stress resistance is increased. Preferably, said plant can be selected from a group consisting of *Arabidopsis thaliana*, rice, rapeseed, wheat, barley, corn, soybean, potato, red bean, oat and millet, but not limited thereto.

In order to achieve another object of the present invention, the present invention provides transgenic seed of the plants that are transformed with the recombinant vector of the present invention. Preferably, said plant can be selected from a group consisting of *Arabidopsis thaliana*, rice, rapeseed, wheat, barley, corn, soybean, potato, red bean, oat and millet, but not limited thereto.

The present invention will now be described in greater detail with reference to the following examples. However, it is only to specifically exemplify the present invention and in no case the scope of the present invention is limited by these examples.

Materials and Methods

Plant Materials and Growth Conditions

*Arabidopsis thaliana* ecotype Ws-2 was used as wild-type for transformation. Seeds were surface-sterilized, chilled at 4° C. for 2 days, and then germinated and grown on 0.8% agar-solidified media containing 1× Murashige and Skoog salts (Murashige T, Skoog F (1962) Physiol Plant 15: 473-497) supplemented with 1% sucrose (pH 5.8 with KOH) under a 16-h-light (22 to 24° C.)/8-h-dark (18 to 20° C.) photoperiod. Soil-grown plants were also grown under the same photoperiod.

Constitutive Expression of AtCYP78A7 in *Arabidopsis*

Genomic fragments containing the coding region of AtCYP78A7 were amplified by Pwo polymerase (Roche, Mannheim, Germany) with a pair of primers using *Arabidopsis* genomic DNA as templates. For easy cloning of PCR products, restriction enzyme sites for KpnI and XbaI were introduced into the primers; 78A7 KpF, 5'-GG GGTACCCATCAACCCAAAATAATGGAGTTGATG-3' (SEQ ID NO: 4); 78A7XbR, 5'-GC TCTAGACATTCTGCAATTCATACCTCTCGACAA-3' (SEQ ID NO: 5). PCR products were cloned into SmaI site of pUC19 vector. The complete nucleotide sequence of the PCR product was determined to check PCR error. KpnI/XbaI fragments of the PCR products were subcloned between CaMV 35S promoter and ocs3' of pART7 (Gleave AP (1992) Plant Mol Biol 20: 1203-1207). A NotI fragments containing the overexpression cassettes from pART7, were subcloned into the binary vector, pART27 (Gleave A P (1992) Plant Mol Biol 20: 1203-1207). The overexpression cassettes in pART27 were transformed into *Agrobacterium* GV3101 by electroporation, and introduced into ecotype Ws-2 plants using the floral dip method (Clough S J, Bent A F (1998) Plant J 16: 735-743). Transgenic plants were selected on MS plates containing kanamycin (40 μg/mL).

Generation of Promoter Construct and GUS Staining Procedures

A genomic fragment (around 2.5 kb in length) containing the promoter region of AtCYP78A7 was obtained from a BAC clone (MYH9) digested with SalI/BamHI. The promoter fragment included a partial ORF of the genes to make translational fusion with GUS gene. The SalI/BamHI fragment was subcloned into pB1101 binary vector. The promoter construct was transformed into *Agrobacterium* GV3101 by electroporation, and introduced into ecotype Ws-2 plants using the floral dip method (Clough S J, Bent AF (1998) Plant J 16: 735-743). Transgenic plants were selected on MS plates containing kanamycicn (40 μg/mL). The homozygous transgenic lines containing the promoter constructs were selected from T3 generation. Plants and plant tissues were stained for GUS according to the method of Stomp (Stomp A-M (1992) In S. R. Gallagher ed, GUS protocols: Using the GUS gene as a reporter of gene expression, Academic Press, San Diego, Calif., pp. 103-113). GUS-stained tissues were dehydrated through an ethanol series.

Reverse Transcription—Polymerase Chain Reaction

Total RNA from plant tissues was purified using TRIzol reagent (Invitrogen, Carlsbad, Calif.). Total RNA (5 μg) was used for first strand cDNA synthesis using the MMLV-reverse transcriptase (Invitrogen). The conditions for PCR amplification were as follows: 96° C., 5 min for initial denaturation followed by 94° C. for 15 sec, 55° C. for 30 sec, and 72° C. for 1 min (total 27 cycles) with 5 min of final extension at 72° C. Transcript encoding tubulin-2 was amplified as a positive control. The primer sequences for RT-PCR are summarized in Table 1.

TABLE 1

Primer sequences used for RT-PCR

| Atg Code | Gene Products | PCR primers (5'→3') Forward | Reverse |
|---|---|---|---|
| At5g09970 | AtCYP78A7 | GGTACGACGGTTC GAGTGGGGTCAGG A (SEQ ID NO: 6) | CATTACTCCATTTA GATTTTAGACCCAC AA (SEQ ID NO: 7) |
| At3g02480 | cold-induced protein kin1 | ATAAAATTCAAAGT GTAAGCAAAAC (SEQ ID NO: 8) | ATTAATTAGAAAAG AAGTCCAAGGT (SEQ ID NO: 9) |
| At5g62490 | ABA-responsive protein (HVA22b) | ATCACGAAGACTAA TAAAACAAAGT (SEQ ID NO: 10) | AACAAATTAACACT TAGGAAAATTG (SEQ ID NO: 11) |
| At2g42530 | cold-responsive protein/cold-regulated protein (cor15b) | AAACAAAAGACTAC ATTGTTGAGA (SEQ ID NO: 12) | TACGTATTTAAAAT GTGCTAGTGAG (SEQ ID NO: 13) |
| At3g50970 | dehydrin xero2 (XERO2) | AAAAGGTATAGCAG AAAAGATTAAA (SEQ ID NO: 14) | CATCATATTATTACA CCACACAAAT (SEQ ID NO: 15) |

TABLE 1-continued

Primer sequences used for RT-PCR

| Atg Code | Gene Products | PCR primers (5'→3') Forward | Reverse |
|---|---|---|---|
| At5g61380 | ABI3-interacting protein 1 (AIP1) | AAGAAGATTAGGTA TGTGAATAGGA (SEQ ID NO: 16) | AACATCTTCTGTTG TTTGATAAGAT (SEQ ID NO: 17) |
| At5g25610 | dehydration-induced protein RD22 | AAAAGTTAGTGGAG AGGAGAAGTAT (SEQ ID NO: 18) | AGATCTATCTAGTA GCTGAACCACA (SEQ ID NO: 19) |
| At5g52310 | dehydration-induced protein RD29A | ATTCTGTTGAAGAG GCTCCAAAATC (SEQ ID NO: 20) | AATACATCAAAGAC GTCAAACAAACA (SEQ ID NO: 21) |
| At1g52400 | AtBG1 (β-glucosidase 1) | TTATATCCAAAGGC ATCTCTTGAGT (SEQ ID NO: 22) | AAACGATCCATAGA ACACACAAACT (SEQ ID NO: 23) |
| | Tubulin-2 | GAGCCTTACAACGC TACTCTGTCTGTC (SEQ ID NO: 24) | ACACCAGACATAGT AGCAGAAATCAAG (SEQ ID NO: 25) |
| | Hygromycin phospho-transferase (hyg) | GATCCGGTCGGCA TCTACTCTATTTC (SEQ ID NO: 26) | CTTGACATTGGGGA GTTTAGCGAGAG (SEQ ID NO: 27) |
| | Ubiquitin | TCATCTAATAACCA GTTCGATTTC (SEQ ID NO: 28) | GACTACAACATCCA GAAGGAGTC (SEQ ID NO: 29) |

Protein Extraction and SDS-PAGE

Five hundreds of mature dried seeds were homogenized with 400 ul of extraction buffer [125 mM Tris-HCl (pH 8.8), 1% SDS, 10% Glycerol, 50 mM sodium sulfite] by using pestle and mortar. After centrifugation, 5 ul of each extract was used for SDS-PAGE (Laemmli UK (1970) Nature 227: 680-685). Protein content was determined by using the Bio-Rad protein assay kit with BSA as the standard.

Dehydration Treatment

Five week-old wild-type and transgenic *Arabidopsis* plants were used for drought-stress treatment. Soil-grown plants were soaked in water for 12 hr and an excess of water was removed, and then were subjected to dehydration stress by withholding irrigation for 18 days. To check if the plants are able to be recovered from dehydration stress, plants were watered again after dehydration stress for 18 days.

RNA Extraction and Microarray Hybridization

Total RNA was isolated from 12-day-old seedlings using TRIzol reagent (Invitrogen). The isolated total RNA was further purified using RNeasy plant mini kit (Qiagen, Germany). cDNAs were prepared from 15 μg of total RNA per sample using Superscript II reverse transcriptase (Invitrogen), and microarray probes labeled with Cy3 and Cy5 were prepared from the cDNA using the Genisphere 3DNA Array 900 DNA labeling kit according to manufacturer's instructions (Genisphere, Montvale, N.J.). The cDNA probes were hybridized to a 29,000-element *Arabidopsis* Oligonucleotide Microarray printed at the University of Arizona using the Qiagen-Operon *Arabidopsis* Genome Array Ready Oligo Set (AROS) Version 3.0 (http://www.ag.arizona.edu/microarray/). Briefly, hybridizations were conducted following the two step protocol: 1) cDNA hybridization to the oligomers spotted on the slides, 2) hybridization of 3-DNA fluorescent dendrimers to cDNAs via the capture sequences incorporated into them during first strand synthesis. All cDNA and fluorescent dye hybridizations were performed in a volume of 35 μL using the SDS-based hybridization buffer provided by the manufacturer. The cDNA hybridizations were performed on a MAUI Hybridization System and MAUI Mixer AO Hybridization Chamber Lids (BioMicro Systems, Salt Lake City) for 18 h at 60° C. The slides were then washed according to the protocol and air dried by centrifugation for 10 min. The 3-DNA hybridizations were performed at 55° C. for 4 hours as described above, except that 0.5 mM DTT was added to the first two wash solutions to protect the fluorochromes from oxidation. Four replicate slides including one dye-swap slide, were generated for each experiment to eliminate dye fluorescence bias. We used three and two slides for the transgenic *Arabidopsis* line #19 and #38, respectively.

Scanning and Data Analysis

After hybridizations, the slides were scanned with Gene-Pix 4000B (Axon Instruments, Union City, Calif.) and the spots were quantified using GenePix Pro 4.0 (Axon Instruments, Union City, Calif., USA). The scanned microarray results were imported into Acuity analysis software 3.0 (Axon Instruments, Union City, Calif.) and normalized using global LOWESS normalization (Yang et al., (2002) Nucleic Acids Res 30:e15). Data files were then created for each experiment which satisfied the following filter [(Sum of Medians>=100) AND (Flags>=0) AND (F635% Sat<3) AND (F532% Sat<3) AND (RgnR2(635/532)>0.6) AND (SNR635>3) AND (SNR532>3)]. This filter eliminates data points which were flagged as bad by GenePix or that had sum of medium less than 100 (very weak) or ones which had pixels less than those of background (not likely to be real spots). The spots which passed these criteria for at least 75% out of the used slides were analyzed. For the comparison of wild-type and transgenic lines, the average of median of ratio for spots which matched these criteria in each dataset were calculated. The resulting two datasets were then clustered using K-means clustering algorithm in Acuity software. Annotations and gene ontology functions for the clones on the microarray were gathered from the website The *Arabidopsis* Information Resource (TAIR, ftp://ftp.arabidopsis.org/home/tair/home/tair/) and classified according to the categories provided by the Gene Ontology Consortium (www.geneontology.org).

Preparation of Transgenic Rice Plant

NotI fragment comprising 35S:AtCYP78A7:3' ocs was obtained from pART27 binary vector. Then, by using pfu DNA polymerase, blunt ends were formed thereto. After the digestion with SmaI, it was cloned into pCAMBIA1301 binary vector. Thus-prepared vector for producing transgenic rice plant was introduced into *Agrobacterium tumefaciens* AGL24 strain using an electric shock method. Said process for producing transgenic rice plants was carried out by using an early transfection method of scutellum tissue. Transgenic rice plant was selected on MS solid medium comprising hygromycin (50 ug/ml).

Genome hybridization method

Isolation of genomic DNA from the rice plant was based on CTAB method. Purified genomic DNA (10 ug) was digested with SacI and subjected to 1% agarose gel electrophoresis. After transferring the digested DNA to a nylon membrane using capillary method, a hybridization reaction was carried out with [$^{32}$P-dCTP]-labeled AtCYP78A7 DNA probe. Conditions for the hybridization reaction and washing were the same as those described in previous art (Kim H B et al. (2003) Journal of Plant Biology. 46:263-270).

Analysis of Water Stress Resistance of the Transgenic Rice Plant

Juvenile form of the rice plant which had been germinated on MS solid medium and grown for about seven days were transferred to soil and allowed to grow in a green house for a month or so. For twelve hours before the water stress treatment, the plant pot was completely soaked in water. After removing the water, no irrigation was applied to the plant for ten days in order to apply water stress to the plant. To determine whether or not the plant can recover from said water stress, the plant was re-watered after ten days.

EXAMPLE 1

RT-PCR Analysis of Expression Profile for Different Types of Tissues

Using RT-PCR, an expression profile was determined for different types of the tissues of the transgenic plant of the present invention. As a result, it was found that AtCYP78A7 gene was expressed in almost all of the tissues, especially strong in floral bud, flower, silique and juvenile plant (see, FIG. 1).

EXAMPLE 2

Analysis Of Expression Using Promoter:GUS

Figure 2:
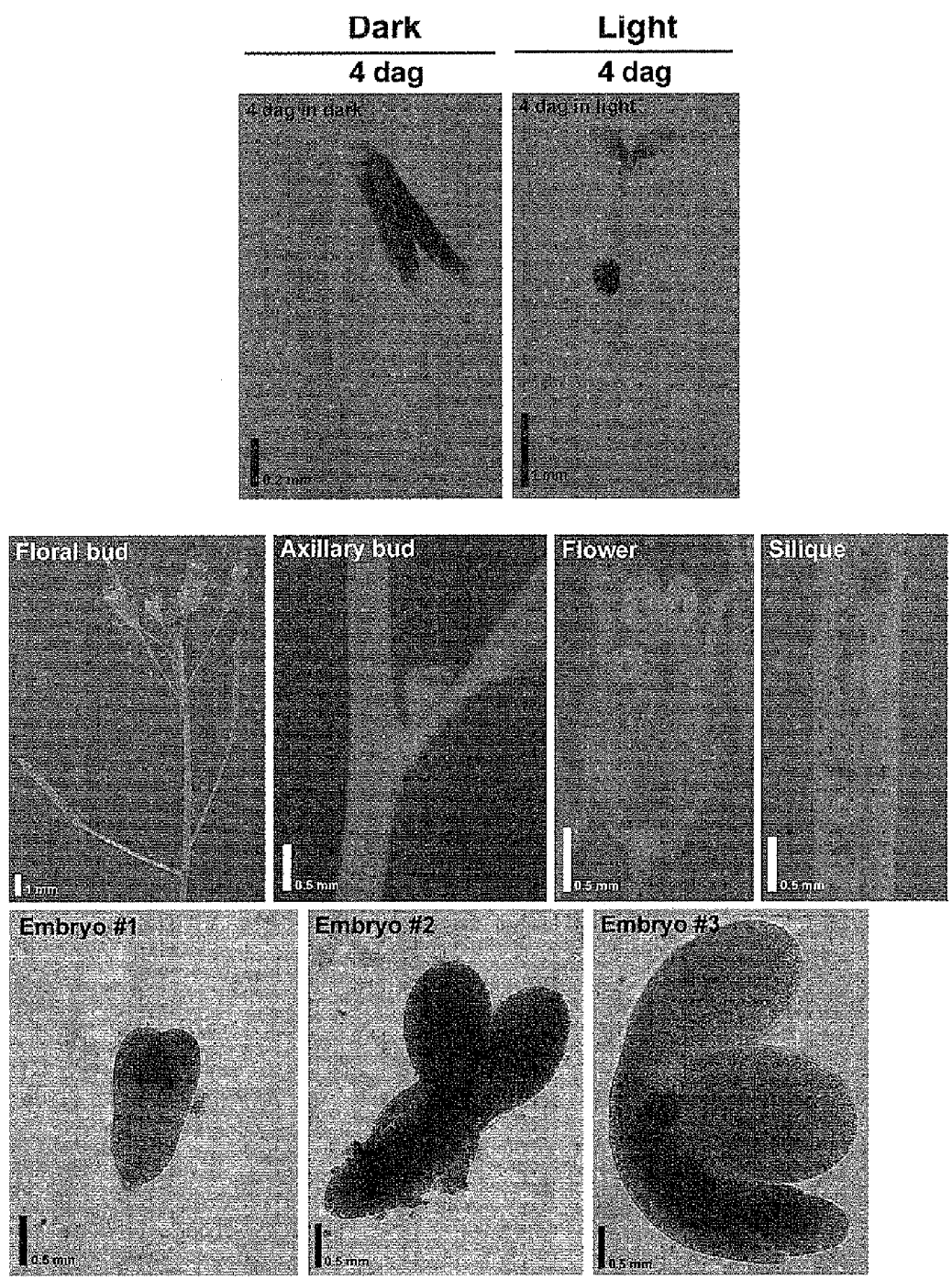
FIG. 2 shows GUS histochemical analysis of AtCYP78A7 expression.

With GUS reporter gene, an expression profile was determined for different types of the tissues of the transgenic plant. As a result, it was found that AtCYP78A7 gene was strongly expressed in cotyledon and apical meristem of dark-germinating/light-germinating seedlings, as well as in floral bud, flower, axillary bud, or embryo under the development (see, FIG. 2).

EXAMPLE 3

Transgenic *Arabidopsis thaliana* which Overexpresses AtCYP78A7 Gene

1) Seed Size, Seed Weight, and Storage Protein Content of the Transgenic Plant

Figure 3:
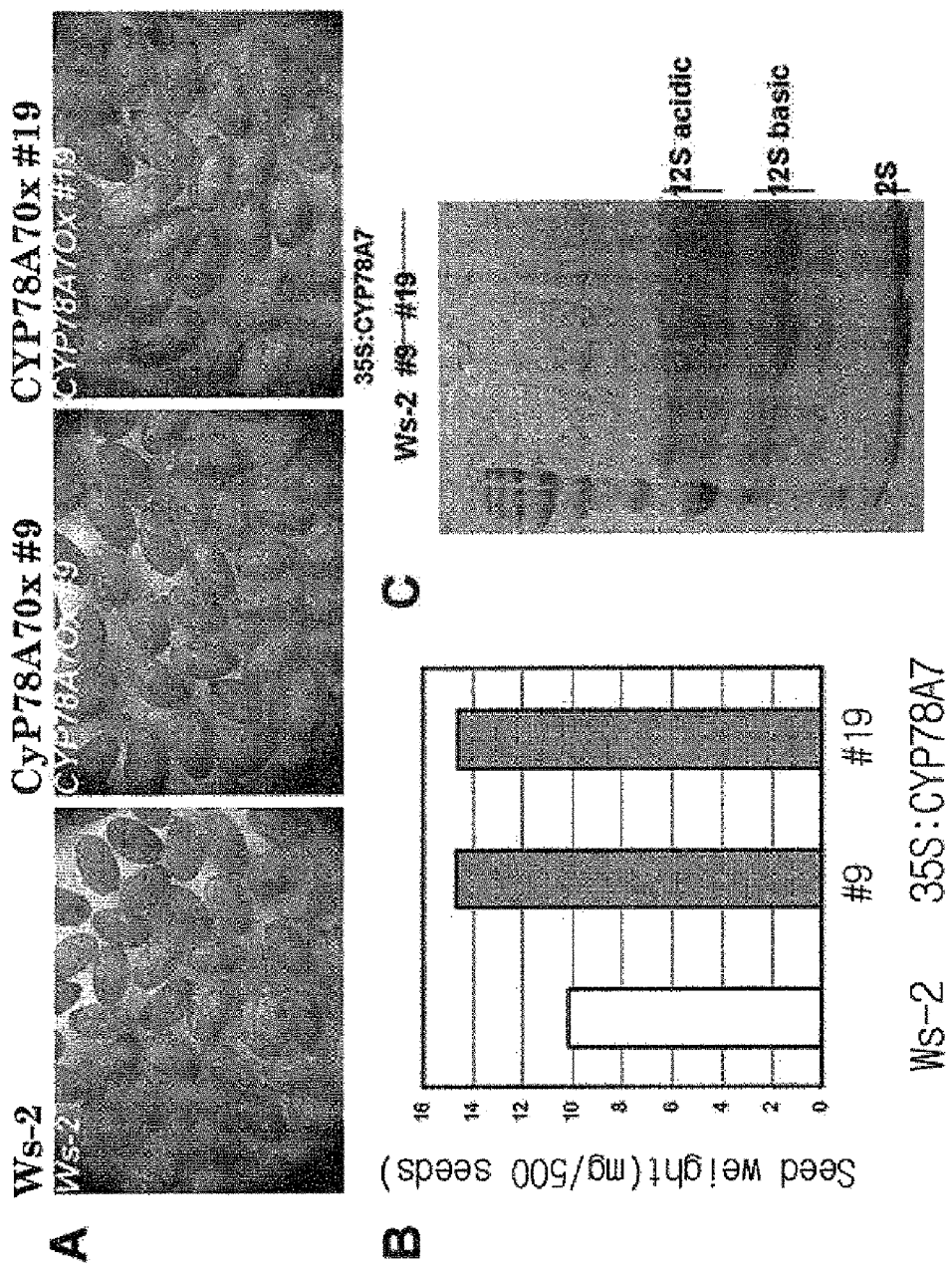
FIG. 3 shows that overexpression of AtCYP78A7 in *Arabidopsis* increases seed size (A), seed weight (B) and contents of seed storage proteins such as 12S globulins and 2S albumins (C).

In case of an overexpressing transgenic plant, the seed size was bigger than the wild-type (Ws-2), as it can be seen from FIG. 3-A. The seed weight was about 50% heavier than that of the wild-type (Ws-2), as it can be seen from FIG. 3-B. In addition, the content of storage protein in the seed such as 12S globulin and 2S albumin, etc. was also increased compared to the wild-type (Ws-2), as it can be seen from FIG. 3-C. Seed weight was measured using an equal number of wild-type (Ws-2) and transgenic seeds (#9 and #19). Whole storage proteins were extracted from an equal number of wild-type (Ws-2) and transgenic seeds (#9 and #19), respectively.

2) Microarray Analysis of the Transgenic Plant

A microarray analysis was carried out using an oligo chip comprising whole genome sequence of *Arabidopsis thaliana*. From the juvenile plant which had been grown for twelve days, total RNA was isolated and then subjected to a microarray analysis, five times that are independent to each other. As a result, it was found that, the seed storage protein of 12S and 2S and the expression of genes which are responsive to ABA, a phytohormone, or to stresses of low temperature/drought were increased in the transgenic plant of the present invention (see, Table 2).

TABLE 2

Microarray analysis revealed that genes encoding seed storage proteins, ABA-responsive or drought/cold-stress-related proteins were up-regulated in the transgenic *Arabidopsis* overexpressing AtCYP78A7.

| Gene category | Gene code | Gene product |
|---|---|---|
| Storage protein genes | At4g28520 | 12S seed storage protein |
| | At4g27150 | 2S seed storage protein 2 |
| | At5g44120 | 12S seed storage protein (CRA1) |
| | At4g27140 | 2S seed storage protein 1 |
| | At4g27160 | 2S seed storage protein 3 |
| ABA-responsive or drought/cold-stress-related genes | At3g02480 | cold-induced protein kin1 |
| | At5g62490 | ABA-responsive protein (HVA22b) |
| | At2g42530 | cold-regulated gene cor15b |
| | At4g19120 | early-responsive to dehydration stress protein (ERD3) |
| | At2g26980 | CBL-interacting protein kinase 3(CIPK3) |
| | At3g50970 | dehydrin xero2 (XERO2)/low-temperature-induced protein LTI30 (LTI30) |
| | At1g56280 | drought-responsive family protein |
| | At1g52400 | glycosyl hydrolase family 1 protein/ beta-glucosidase (AtBG1) |
| | At5g61380 | ABI3-interacting protein 1 (AIP1) |

Figure 4:
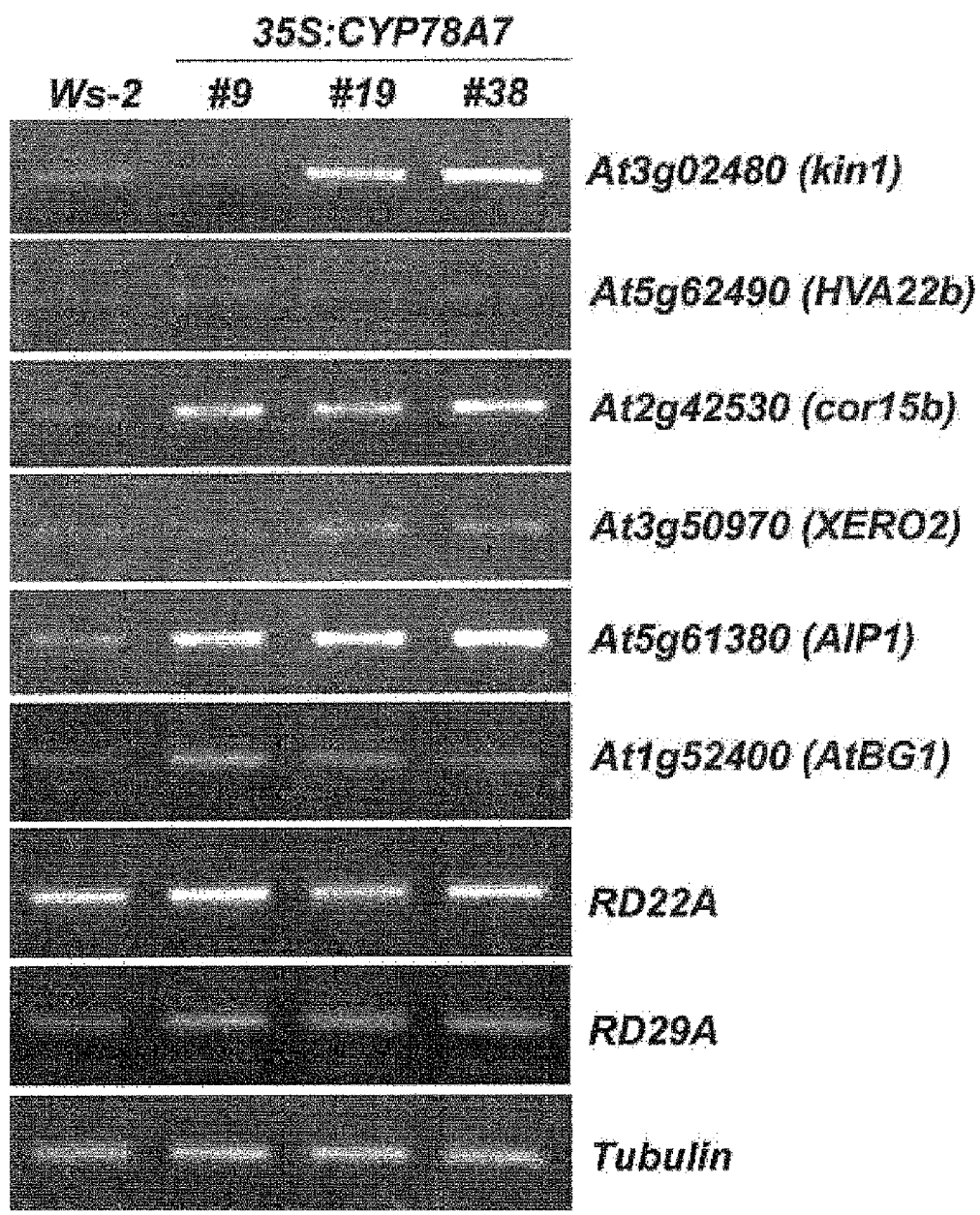
FIG. 4 shows semi-quantitative RT-PCR of ABA-responsive, drought/cold-stress-related genes.

In order to determine any increase in the expression of the above-described genes in the transgenic plant of the present invention, RNAs were isolated from the wild-type (Ws-2) and the transgenic plant (lines #9, #19 and #38 of 35S: AtCYP78A7), respectively. After the RT-PCR, it was found that their expressions were all increased in the transgenic plant of the present invention (see, FIG. 4).

3) Water Stress Resistance of the Transgenic Plant of the Present Invention

Figure 5:
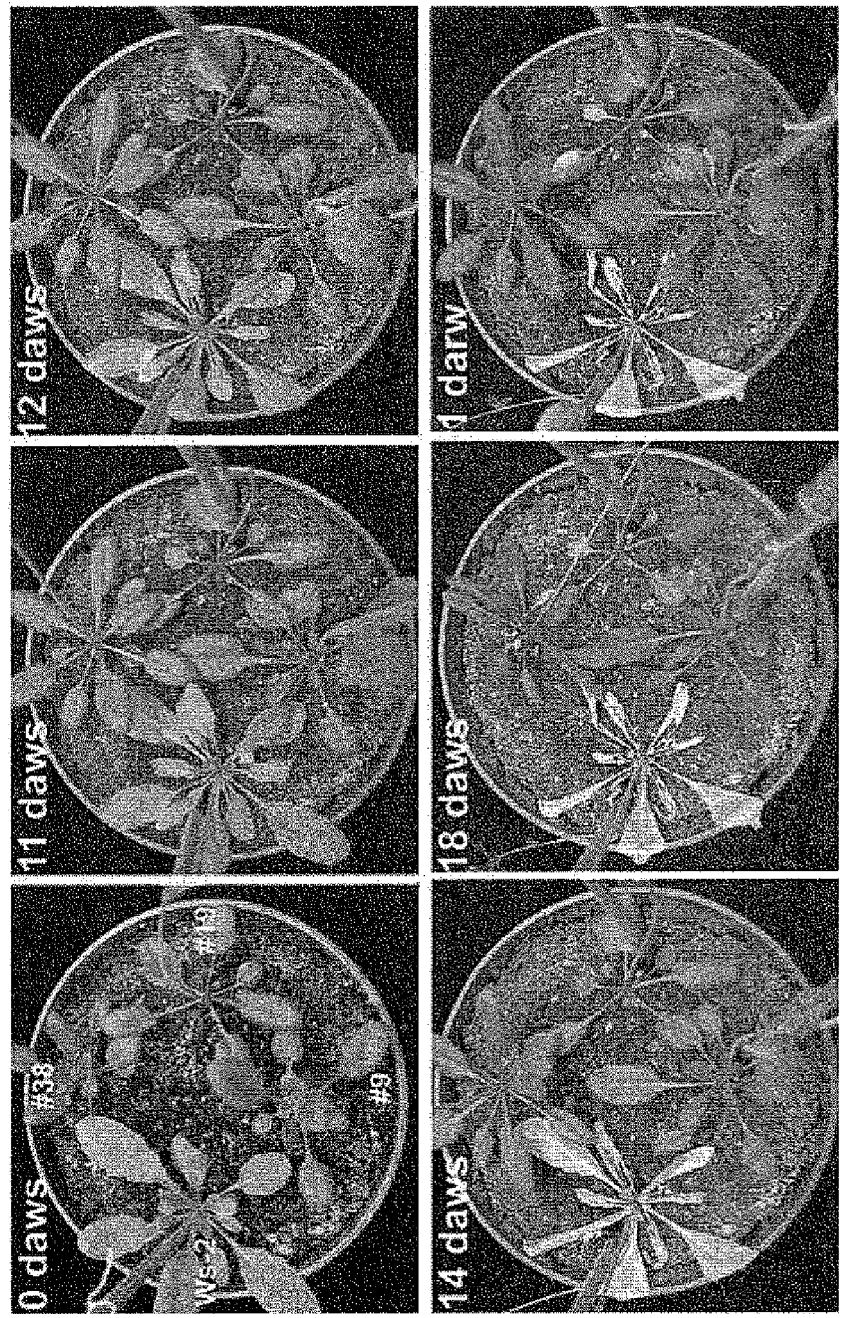
FIG. 5 shows comparison of drought-stress response between wild-type and the transgenic *Arabidopsis*. Numbers indicate independent transgenic lines overexpressing AtCYP78A7. daws, days after water stress; darw, days after re-watering.

Based on the results obtained from the above-described microanalysis results, water stress resistance of the transgenic plant of the present invention was investigated. For the wild-type, it was found that the plants started to get withered twelve days after the water stress treatment and then completely died on the eighteenth day. On the other hand, for the transgenic plant of the present invention (lines #9, #19 and #38 of 35S: AtCYP78A7), it was found that the plants started to get withered eighteen days after the water stress treatment and it completely recovered the water stress once watered again. The wild-type plant never recovered (see, FIG. 5).

EXAMPLE 4

Figure 6:
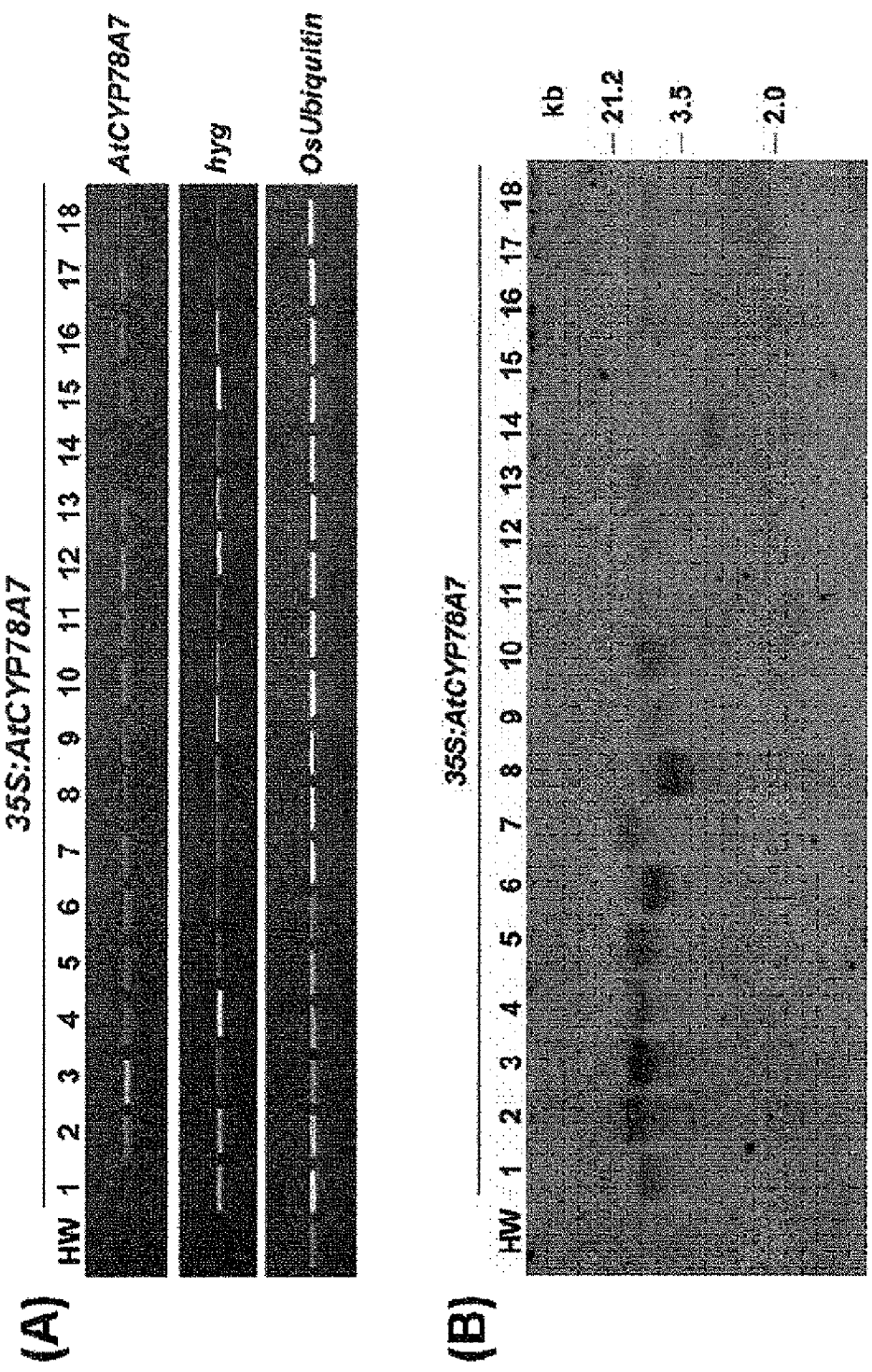
FIG. 6 shows the results of PCR (A) and genome hybridization reaction (B) in order to confirm the expression of AtCYP78A7 gene in the transgenic rice plant which overexpresses AtCYP78A7. Numbers shown in the figure indicate the number of the individual transgenic rice plant which overexpresses AtCYP78A7. HW (Hwayoung) is a control rice group.
Figure 7:
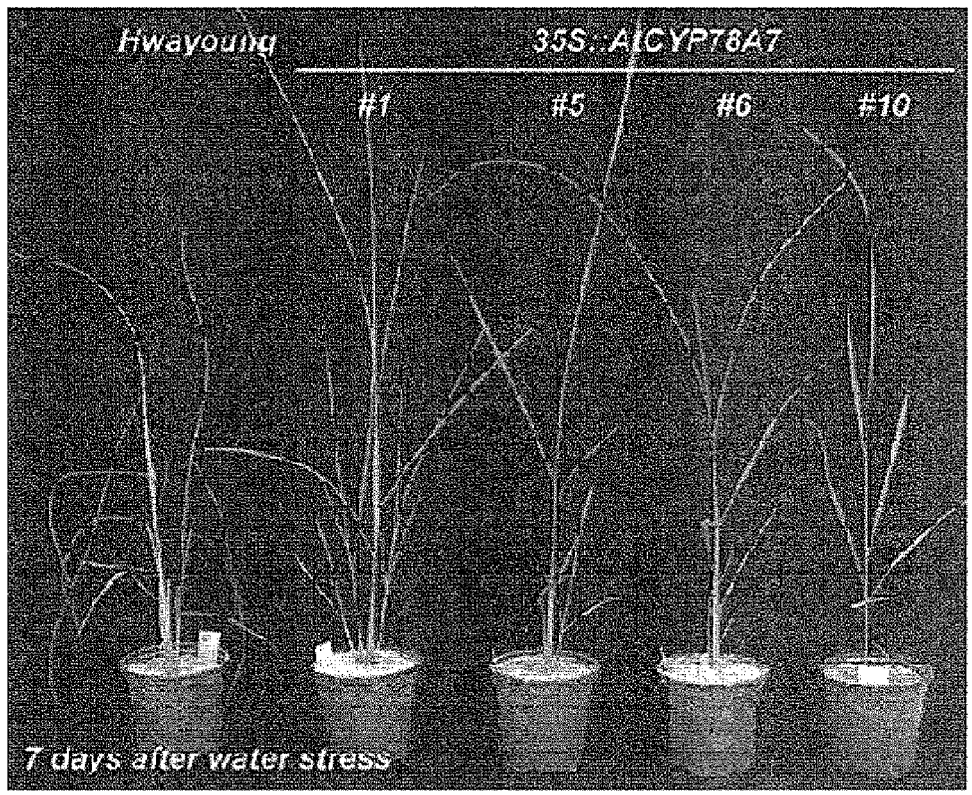
FIG. 7 shows the results of testing water stress resistance of some of the transgenic rice plants that have been produced in the present invention.
Figure 7:
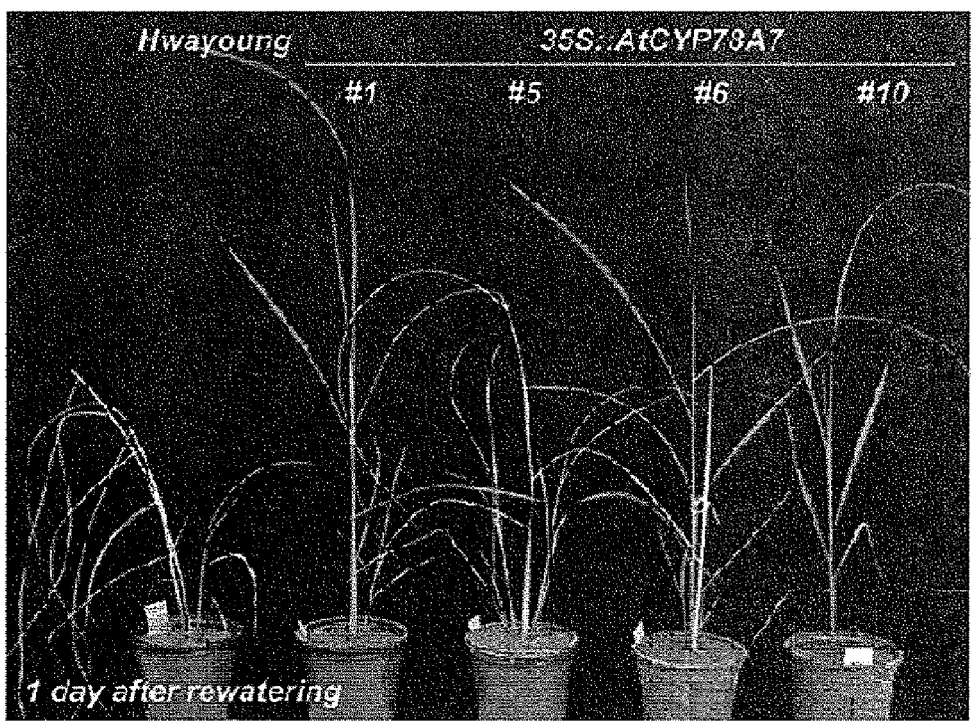

Preparation of the Transgenic Rice Plant which Overexpresses AtCYP78A7 and a Test for Measuring Water Stress Resistance of the Plant Eighteen individual lines of the transgenic rice plant which overexpresses AtCYP78A7 were prepared. For all the lines of the transgenic rice plant prepared, the expression of a selection marker gene (hyg) was confirmed (see, FIG. 6-A). Except line #14, AtCYP78A7 gene expression was confirmed for all the lines of the transgenic rice plant (see, FIG. 6-A). Genomic DNA was extracted from thus-prepared transgenic rice plants and a genome hybridization reaction was carried out using AtCYP78A7 gene as a probe. As a result, it was confirmed that AtCYP78A7 gene which had been introduced into the plant was successfully incorporated into the genome of the rice plant (see, FIG. 6-B). For some of thus-prepared transgenic rice plants, a test for measuring water stress resistance was carried out. As a result, it was found that the wild-type plants (Hwayoung) started to get withered seven days after the water stress treatment, while the transgenic plant of the present invention did not get withered (see, left panel of FIG. 7). After the water stress treatment for ten days, the plants were rewatered. The wild-type plants could not recover, but all of the transgenic rice plants of the present invention recovered nicely to their normal state, except line #5 (see, right panel of FIG. 7).

Figure 8:
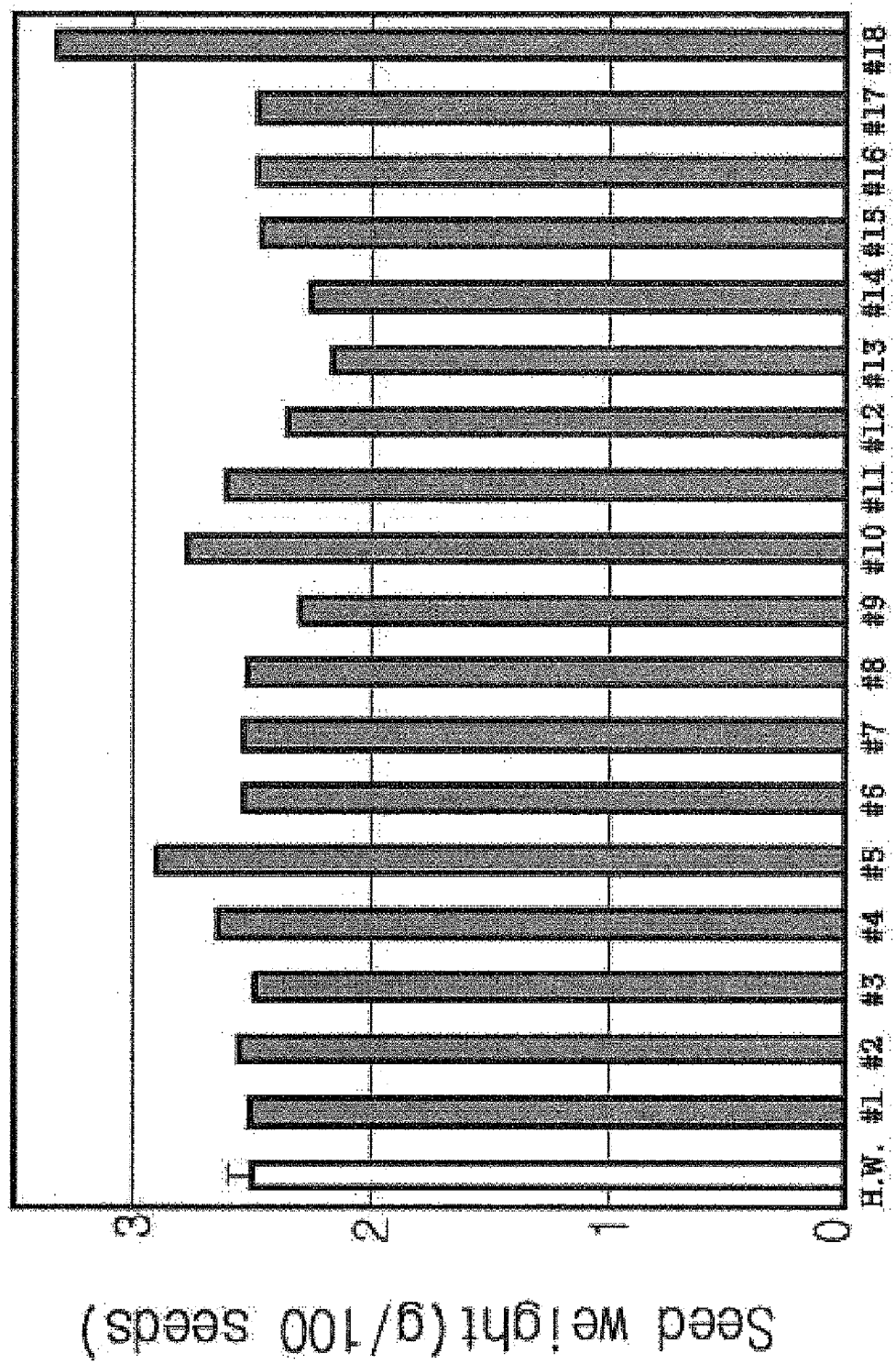
FIG. 8 shows the results of weighing the seeds of the transgenic rice plants that have been produced in the present invention (i.e., for one hundred seeds). Numbers shown in the figure indicate the number of the individual transgenic rice plant which overexpresses AtCYP78A7. HW (Hwayoung) is a control rice group.

For the eighteen individual transgenic rice plants which overexpress AtCYP78A7, weight of one hundred seeds was measured, respectively. As a result, it was found that for lines #5, #10 and #18 seed weight was 10-33% heavier than that of the non-transgenic plant (see, FIG. 8).

The invention claimed is:

1. A method of increasing seed size or storage protein content in seed or increasing water stress resistance of a plant, said method comprising:
   (i) transforming a plant cell with a recombinant plant expression vector comprising a polynucleotide encoding a cytochrome P450 protein having the amino acid sequence of SEQ ID NO: 1;
   (ii) regenerating a transgenic plant from said plant cell; and
   (iii) selecting for transgenic plants having increased water stress resistance or increased size seed or storage protein content in seed, relative to a control plant not comprising the expression vector.

2. The method according to claim 1, characterized in that said plant is selected from a group consisting of *Arabidopsis thaliana*, rice, rapeseed, wheat, barley, corn, soybean, potato, red bean, oat and millet.

3. A plant having increased seed size or storage protein content in seed or increased water stress resistance, wherein said plant is produced by the method according to claim 1.

4. The plant according to claim 3, characterized in that said plant is selected from a group consisting of *Arabidopsis thaliana*, rice, rapeseed, wheat, barley, corn, soybean, potato, red bean, oat and millet.

5. A transgenic seed of the plant according to claim 3, wherein said seed comprises a recombinant plant expression vector comprising a polynucleotide encoding a cytochrome P450 protein having the amino acid sequence of SEQ ID NO:1.

* * * * *

SEQUENCE LISTING

<160> NUMBER OF SEQ ID NOS: 29

<210> SEQ ID NO 1
<211> LENGTH: 536
<212> TYPE: PRT
<213> ORGANISM: Arabidopsis thaliana

<400> SEQUENCE: 1

```
Met Glu Leu Met Asn Leu Ala Ser Lys Glu Thr Ser Tyr Trp Met Ile
 1               5                  10                  15

Ala Leu Pro Ala Gly Phe Gly Ser Gln Asn Leu His Asp Val Ser Thr
            20                  25                  30

Leu Gly Tyr Leu Phe Leu Ala Val Val Phe Leu Ser Ile Val Thr Trp
        35                  40                  45

Ala Leu Ala Gly Gly Gly Gly Val Ala Trp Lys Asn Gly Arg Asn Arg
    50                  55                  60

Leu Gly Arg Val Ala Ile Pro Gly Pro Arg Gly Ile Pro Val Phe Gly
65                  70                  75                  80

Ser Leu Phe Thr Leu Ser Arg Gly Leu Ala His Arg Thr Leu Ala Ala
                85                  90                  95
```

```
Met Ala Trp Ser Arg Ala Asn Thr Glu Ile Met Ala Phe Ser Leu Gly
                100                 105                 110
Ser Thr Pro Val Ile Val Ala Ser Glu Pro Asn Ile Ala Arg Glu Ile
            115                 120                 125
Leu Met Ser Pro His Phe Ala Asp Arg Pro Val Lys Gln Ser Ala Lys
        130                 135                 140
Ser Leu Met Phe Ser Arg Ala Ile Gly Phe Ala Pro Asn Gly Thr Tyr
145                 150                 155                 160
Trp Arg Met Leu Arg Arg Ile Ala Ser Thr His Leu Phe Ala Pro Arg
                165                 170                 175
Arg Ile Leu Ala His Glu Ala Gly Arg Gln Leu Asp Cys Ala Glu Met
            180                 185                 190
Val Lys Ala Val Ser Val Glu Gln Asn Gly Ala Gly Ser Val Val Leu
        195                 200                 205
Arg Lys His Leu Gln Leu Ala Ala Leu Asn Asn Ile Met Gly Ser Val
210                 215                 220
Phe Gly Arg Arg Tyr Asp Pro Leu Ala Gln Lys Glu Asp Leu Asp Glu
225                 230                 235                 240
Leu Thr Ser Met Val Arg Glu Gly Phe Glu Leu Leu Gly Ala Phe Asn
                245                 250                 255
Trp Ser Asp Tyr Leu Pro Trp Leu Gly Tyr Phe Tyr Asp Ser Ile Arg
            260                 265                 270
Leu Asn Gln Arg Cys Ser Asp Leu Val Pro Arg Ile Arg Thr Leu Val
        275                 280                 285
Lys Lys Ile Ile Asp Glu His Arg Val Ser Asn Ser Glu Lys Lys Arg
                295                 300
290
Asp Ile Gly Asp Phe Val Asp Val Leu Leu Ser Leu Asp Gly Asp Glu
305                 310                 315                 320
Lys Leu Gln Glu Asp Asp Met Ile Ala Val Leu Trp Glu Met Ile Phe
                325                 330                 335
Arg Gly Thr Asp Thr Thr Ala Leu Leu Thr Glu Trp Thr Met Ala Glu
            340                 345                 350
Leu Val Leu Asn Pro Asn Val Gln Thr Lys Leu Arg Asp Glu Ile Leu
        355                 360                 365
Thr Ala Val Gly Asp Gly Ala Asp Gly Asp Val Ala Asp Ala Asp Leu
        370                 375                 380
Ala Lys Leu Pro Tyr Leu Asn Ala Val Val Lys Glu Thr Leu Arg Leu
385                 390                 395                 400
His Pro Pro Gly Pro Leu Leu Ser Trp Ala Arg Leu Ser Thr Ser Asp
                405                 410                 415
Val Gln Leu Ser Asn Gly Met Val Ile Pro Lys Gly Thr Thr Ala Met
            420                 425                 430
Val Asn Met Trp Ala Ile Thr His Asp Gln Thr Val Trp Ser Asp Pro
        435                 440                 445
Leu Lys Phe Asp Pro Glu Arg Phe Thr Gly Asn Ala Asp Met Asp Ile
        450                 455                 460
Arg Gly Gly Asp Leu Arg Leu Ala Pro Phe Gly Ala Gly Arg Arg Val
465                 470                 475                 480
Cys Pro Gly Lys Asn Met Gly Leu Ala Thr Val Thr Arg Trp Val Ala
                485                 490                 495
Glu Leu Val Arg Arg Phe Glu Trp Gly Gln Asp Gln Thr Glu Pro Val
            500                 505                 510
Asp Leu Gly Glu Val Leu Lys Leu Ser Cys Glu Met Glu His Pro Leu
        515                 520                 525
```

Arg Ala Val Val Thr Glu Ile Phe
    530                 535

<210> SEQ ID NO 2
<211> LENGTH: 1611
<212> TYPE: DNA
<213> ORGANISM: Arabidopsis thaliana

<400> SEQUENCE: 2

```
atggagttga tgaatttggc ttcaaaagaa acaagctatt ggatgattgc actgcctgcc      60
ggttttggat cccaaaacct acatgatgtt tccaccctag ctatctatt ccttgccgtc     120
gttttctct ctatagtcac gtgggctctc gccggaggcg gtggtgtcgc ttggaagaac     180
ggccgtaacc ggttgggtcg tgtcgcgatc cctggtcctc gtggcatacc agtattcggc     240
agtcttttca ctctcagccg aggcttggct catcggacgt tagcagccat ggcttggagc     300
cgagccaaca ctgagattat ggcttttagc cttggttcaa cgccggttat cgtggcttct     360
gaaccaaaca tagctcgtga gattctgatg tcgcctcact tcgcggaccg gccggttaag     420
cagtctgcta agagcctcat gttcagccga gccataggtt tcgccccaaa cgggacttac     480
tggcgcatgt taagaaggat cgcatcgact cacctatttg ctcctcggcg tatcttagca     540
cacgaagctg ggcgccagct agactgcgct gaaatggtga agctgtgtc agtgagcaa      600
aacggcgctg atcagtcgt tttaaggaaa cacttacaac tagccgcctt gaacaacatc     660
atggaagtg tttttgggag aagatacgat cctctggctc agaaagagga tcttgatgag     720
cttacatcaa tggttaggga agggttcgag cttttgggtg cttttaattg gtctgattat     780
cttccatggc tcggttattt ctacgactca attcgtttaa accaacgttg ctcagatctc     840
gtccctcgaa ttagaaccct cgtcaagaaa atcatcgacg aacatcgagt tagtaactct     900
gagaagaaaa gagacattgg agattttgtt gatgtcttat tgtctttaga cggtgatgag     960
aaacttcaag aagatgacat gatcgccgtt ttatgggaga tgattttttcg agggacagat    1020
acaacggcgt tattaacgga gtggaccatg gccgagctag tactgaaccc taacgtgcaa    1080
accaagttac gagacgagat tttaactgct gtgggcgacg cgccgacgg agacgtggca    1140
gatgctgacc tggcaaaact cccgtaccta aacgcagtgg tgaaggaaac tctaaggctg    1200
catcctcctg accactgct tcatgggct cgtctttcca cgtcagacgt ccagctcagc    1260
aatggcatgg tgattccaaa gggaactaca gcgatggtca acatgtgggc tataacccac    1320
gaccagactg tatggtccga cccgctaaag tttgacccgg agagattcac tgggaatgct    1380
gacatggata ttcgtggtgg ggatctaagg cttgcaccgt ttggagccgg taggagagtg    1440
tgtccgggga gaacatggg gctagctact gtgactcggt gggtggctga gttggtacga    1500
cggttcgagt ggggtcagga tcagaccgag ccagttgatc ttggtgaggt cttgaagctt    1560
tcttgtgaga tggagcatcc gttacgtgcc gttgtaacgg aaatatttta a            1611
```

<210> SEQ ID NO 3
<211> LENGTH: 2416
<212> TYPE: DNA
<213> ORGANISM: Arabidopsis thaliana

<400> SEQUENCE: 3

```
gtcgacccgc cccattccct gccaaacctc ccttcttcac cattcacact tttttctttt      60
ctttgaccaa ttgaaaaatt atttatatac attaattaat agttaaaagt aaacaaaatg     120
agaagcacca atctatttg gttaattttc catttagatg taactttcat gatagatgtt     180
```

```
gagattcaaa cctattacct aatatgttaa gcatgaagaa tggatgattt ggtgcatccc    240
aacctcggcc tctaagattc cacaacggat tcctctaact ttcaccaatt tgttaggctt    300
ttttattcaa tattttcaca agcattatct tcaaagaaaa cggtaaacga cgagctagaa    360
atatgcaaca tacaaattgc atgagacgtt tagttaactg gttttctaat gtgatttgat    420
tgtctcttgt tcttattatt aaagattata tattctcgta aatgaaaatt gttttatgtg    480
aaacggcatt tgcttaatct aacgcctaag taaaaatcta gtgttctaca tcatgtgttc    540
gaattagatc tatgttcaaa atgtgcgatg tgtttttaca tattattatt gtatatacta    600
ctgactacag tttgtcgtag tatacgtctt atagaaattt tgattgagca ttgaggagtt    660
cttttgagta atttgtatgt tgctatttag attatgtatt tgcaaattaa attgttagat    720
ttgtacgtcg taaacgatat aaatatttta aatatgataa gtgataaata ggaaaccatt    780
tccattactt aacatcattg atacaataca aagatttgaa tctcacgata agaattggtt    840
gctttctcta ttaggatcac tataaaaact tgtgatcaac gagttttaat gaataatatc    900
agtatttttt gtaaaaaaaa tagcgataaa aatattatat taatcgttga ttaaatataa    960
tatattgtta cgatcggata aaaaatatta atttattaat gatcgatcga taaatctatt    1020
atttaataaa tagattatat aagacaaata aatagattat ataagacaaa aatggtcaaa    1080
cgatattaaa tataaataaa tacatacatc gtgttttcg agttggatat atgatcgtta    1140
attaaatata ttgttacgat catataaaaa gatcatttct tagtaatagt tcgggatgga    1200
ttggtgttgt tcctctacgc ctaggacacc agaatatcga accatgaata tcaatcgata    1260
aatatattat ttaaataatc gcttatatac gacaaaaaaa atcaaaatga tattgaatta    1320
atatagataa atacatacac aaatctggat gcgatagcaa aaacctagaa cgtctatttt    1380 ttttttttgca tttcctgaat ttttttttaa tcagccatat actcataagt tttacaaaaa    1440
tgtctccttt atctcatcca ctttaaaatt acttattcat caaattttaa cagtagaaga    1500
cttaaaacta cagtttctta gcaaaaaata aataatttac atagtcccca attatatact    1560
tcgaaaacta tatattacta aaagctcaaa tataatgttc aattatactc tcatggaaaa    1620
ttataattct gttctactac aaactcaaaa aatatgaaga taattaatca gggcaagtat    1680
ctcgctgcac gtcacaacta tctaaagcca tcgatatcta taaccgacta atattctttc    1740
ttctctaaag aacatattca ttggtttgtc ctttcgtatt ctctaagccg aaatatacgg    1800
actcattgaa ttctttttc ggtttaacga acctcattga attctcacat cgatgcaaag    1860
taacatcaca acccaagaaa aaaacggtgc aaacataatt aaatatagct aattaagaaa    1920
aacaaaataa aaatgccgaa ttcattgtca taacgccctc tttcacacac atatctttca    1980
tttcatccaa caccaaacca attcatgcga cccacctcct ccctccacgt gaatctctcc    2040
caattttaac cttgccaatt ttcctatatt ttacatcaac attacttata tataaacggg    2100
ataaattata tagaatcatt tcaaaaccga cgtctttctt cccatgcatt gcgcatttaa    2160
ttaacgctgc caaaacatac atgtggatat atatatagtt tttttatata tagatgtacc    2220
tttaccttca acttctccat tgttcttctc caagtacttc tctcttcaac caaaaaaaaa    2280
gagtactttc cttctcatag gatttttttg ctttctcttg aaaaaccttt tgttattgtt    2340
attggttcgt acgttgttca ttatttgaca agaaacaaga ttacaaaaaa aaaaagtaca    2400
tcaacccaaa ataatg                                                    2416
```

<210> SEQ ID NO 4
<211> LENGTH: 35
<212> TYPE: DNA

```
<213> ORGANISM: Artificial Sequence
<220> FEATURE:
<223> OTHER INFORMATION: synthetic

<400> SEQUENCE: 4
ggggtaccca tcaacccaaa ataatggagt tgatg                              35

<210> SEQ ID NO 5
<211> LENGTH: 35
<212> TYPE: DNA
<213> ORGANISM: Artificial Sequence
<220> FEATURE:
<223> OTHER INFORMATION: synthetic

<400> SEQUENCE: 5
gctctagaca ttctgcaatt catacctctc gacaa                             35

<210> SEQ ID NO 6
<211> LENGTH: 27
<212> TYPE: DNA
<213> ORGANISM: Arabidopsis thaliana

<400> SEQUENCE: 6
ggtacgacgg ttcgagtggg gtcagga                                      27

<210> SEQ ID NO 7
<211> LENGTH: 30
<212> TYPE: DNA
<213> ORGANISM: Arabidopsis thaliana

<400> SEQUENCE: 7
cattactcca tttagatttt agacccacaa                                   30

<210> SEQ ID NO 8
<211> LENGTH: 25
<212> TYPE: DNA
<213> ORGANISM: Arabidopsis thaliana

<400> SEQUENCE: 8
ataaaattca aagtgtaagc aaaac                                        25

<210> SEQ ID NO 9
<211> LENGTH: 25
<212> TYPE: DNA
<213> ORGANISM: Arabidopsis thaliana

<400> SEQUENCE: 9
attaattaga aaagaagtcc aaggt                                        25

<210> SEQ ID NO 10
<211> LENGTH: 25
<212> TYPE: DNA
<213> ORGANISM: Arabidopsis thaliana

<400> SEQUENCE: 10
atcacgaaga ctaataaaac aaagt                                        25

<210> SEQ ID NO 11
<211> LENGTH: 25
<212> TYPE: DNA
<213> ORGANISM: Arabidopsis thaliana

<400> SEQUENCE: 11
aacaaattaa cacttaggaa aattg                                        25
```

```
<210> SEQ ID NO 12
<211> LENGTH: 24
<212> TYPE: DNA
<213> ORGANISM: Arabidopsis thaliana

<400> SEQUENCE: 12
aaacaaaaga ctacattgtt gaga                                          24

<210> SEQ ID NO 13
<211> LENGTH: 25
<212> TYPE: DNA
<213> ORGANISM: Arabidopsis thaliana

<400> SEQUENCE: 13
tacgtattta aaatgtgcta gtgag                                         25

<210> SEQ ID NO 14
<211> LENGTH: 25
<212> TYPE: DNA
<213> ORGANISM: Arabidopsis thaliana

<400> SEQUENCE: 14
aaaaggtata gcagaaaaga ttaaa                                         25

<210> SEQ ID NO 15
<211> LENGTH: 25
<212> TYPE: DNA
<213> ORGANISM: Arabidopsis thaliana

<400> SEQUENCE: 15
catcatatta ttacaccaca caaat                                         25

<210> SEQ ID NO 16
<211> LENGTH: 25
<212> TYPE: DNA
<213> ORGANISM: Arabidopsis thaliana

<400> SEQUENCE: 16
aagaagatta ggtatgtgaa tagga                                         25

<210> SEQ ID NO 17
<211> LENGTH: 25
<212> TYPE: DNA
<213> ORGANISM: Arabidopsis thaliana

<400> SEQUENCE: 17
aacatcttct gttgtttgat aagat                                         25

<210> SEQ ID NO 18
<211> LENGTH: 25
<212> TYPE: DNA
<213> ORGANISM: Arabidopsis thaliana

<400> SEQUENCE: 18
aaaagttagt ggagaggaga agtat                                         25

<210> SEQ ID NO 19
<211> LENGTH: 25
<212> TYPE: DNA
<213> ORGANISM: Arabidopsis thaliana

<400> SEQUENCE: 19
agatctatct agtagctgaa ccaca                                         25
```

```
<210> SEQ ID NO 20
<211> LENGTH: 25
<212> TYPE: DNA
<213> ORGANISM: Arabidopsis thaliana

<400> SEQUENCE: 20
attctgttga agaggctcca aaatc                                          25

<210> SEQ ID NO 21
<211> LENGTH: 27
<212> TYPE: DNA
<213> ORGANISM: Arabidopsis thaliana

<400> SEQUENCE: 21
aatacatcaa agacgtcaaa caaaaca                                        27

<210> SEQ ID NO 22
<211> LENGTH: 25
<212> TYPE: DNA
<213> ORGANISM: Arabidopsis thaliana

<400> SEQUENCE: 22
ttatatccaa aggcatctct tgagt                                          25

<210> SEQ ID NO 23
<211> LENGTH: 25
<212> TYPE: DNA
<213> ORGANISM: Arabidopsis thaliana

<400> SEQUENCE: 23
aaacgatcca tagaacacac aaact                                          25

<210> SEQ ID NO 24
<211> LENGTH: 27
<212> TYPE: DNA
<213> ORGANISM: Arabidopsis thaliana

<400> SEQUENCE: 24
gagccttaca acgctactct gtctgtc                                        27

<210> SEQ ID NO 25
<211> LENGTH: 27
<212> TYPE: DNA
<213> ORGANISM: Arabidopsis thaliana

<400> SEQUENCE: 25
acaccagaca tagtagcaga aatcaag                                        27

<210> SEQ ID NO 26
<211> LENGTH: 26
<212> TYPE: DNA
<213> ORGANISM: Arabidopsis thaliana

<400> SEQUENCE: 26
gatccggtcg gcatctactc tatttc                                         26

<210> SEQ ID NO 27
<211> LENGTH: 26
<212> TYPE: DNA
<213> ORGANISM: Arabidopsis thaliana

<400> SEQUENCE: 27
cttgacattg gggagtttag cgagag                                         26
```

```
<210> SEQ ID NO 28
<211> LENGTH: 24
<212> TYPE: DNA
<213> ORGANISM: Arabidopsis thaliana

<400> SEQUENCE: 28
tcatctaata accagttcga tttc                                              24

<210> SEQ ID NO 29
<211> LENGTH: 23
<212> TYPE: DNA
<213> ORGANISM: Arabidopsis thaliana

<400> SEQUENCE: 29
gactacaaca tccagaagga gtc                                               23
```